US 6,656,312 B1

(12) United States Patent
Schmitz et al.

(10) Patent No.: US 6,656,312 B1
(45) Date of Patent: Dec. 2, 2003

(54) APPARATUS AND PROCESS FOR APPLYING DISCRETE PORTIONS OF A WEB MATERIAL ONTO RECEIVING WEB

(75) Inventors: Christoph Johann Schmitz, Euskirchen-Stotzheim (DE); Uwe Schneider, Rheinbach (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/889,052

(22) PCT Filed: Jan. 12, 2000

(86) PCT No.: PCT/US00/00779

§ 371 (c)(1),
(2), (4) Date: Jul. 11, 2001

(87) PCT Pub. No.: WO00/41664

PCT Pub. Date: Jul. 20, 2000

(30) Foreign Application Priority Data

Jan. 16, 1999 (EP) .............................. 99100768

(51) Int. Cl.$^7$ .......................... A61F 13/15; B32B 31/10
(52) U.S. Cl. ................. 156/265; 156/164; 156/235; 156/297; 156/519; 156/522; 156/552; 156/556
(58) Field of Search .................. 156/164, 230, 156/235, 264, 265, 519, 522, 552, 556, 297, 299, 464, 543

(56) References Cited

U.S. PATENT DOCUMENTS

| 4,578,133 A | 3/1986 | Oshefsky et al. |
| 5,340,426 A | * 8/1994 | Takahashi et al. .......... 156/264 |
| 5,660,665 A | 8/1997 | Jalonen |
| 5,759,340 A | 6/1998 | Boothe et al. |

FOREIGN PATENT DOCUMENTS

| WO | WO 96/23470 A1 | 8/1996 |

OTHER PUBLICATIONS

PCT International Search Report for PCT/US00/00779; date of mailing: Mar. 31, 2000.

* cited by examiner

Primary Examiner—Adrienne C. Johnstone
Assistant Examiner—Barbara J Musser
(74) Attorney, Agent, or Firm—Jack L. Oney, Jr.; Michael S. Kolodesh; Ken K. Patel

(57) ABSTRACT

The present invention relates to an apparatus for applying discrete portions (10) of a web material onto a receiving web (7) comprising: a primary axis of rotation and an attachment zone to an average radial distance, $R_1$, from the primary axis of rotation; transfer elements (6) rotatable about the axis, the transfer elements receiving a second web (2) at a radial distance, $R_2$, from the primary axis wherein the radial distance $R_1$, is greater than the radial distance $R_2$; a means for displacing the transfer elements (6) so that the second web (2) is moved immediately adjacent to the attachment zone; and an attachment surface (10) rotatable about the primary axis and through the attachment zone, for transporting the receiving web (7) about the primary axis, whereby discrete portions (10) of the second web (2) are attached to the receiving web (7) in the attachment zone, forming a composite web comprising the receiving web (7) and discrete portions (10) of the second web (2). The present invention also relates to a process for applying discrete portions (10) of a web material onto a receiving web (7) using the above described apparatus.

7 Claims, 4 Drawing Sheets

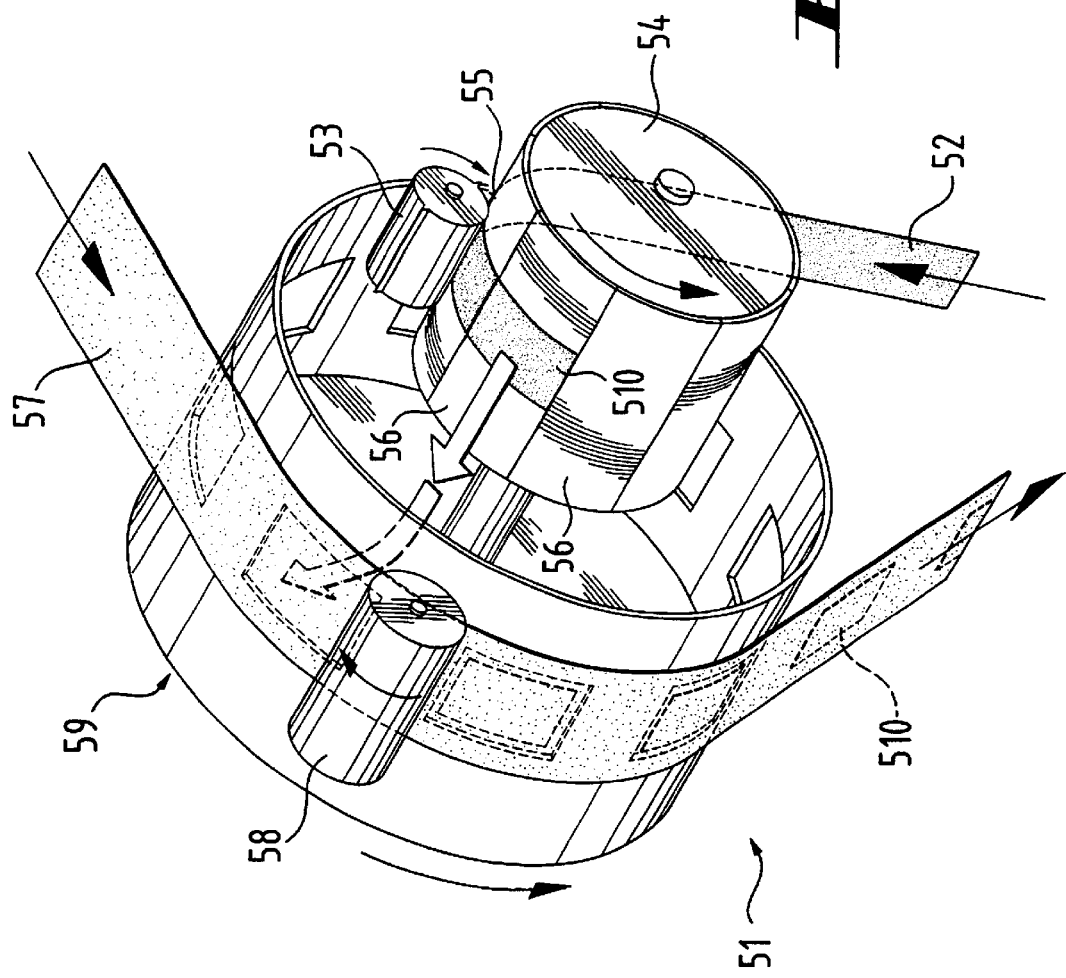

APPARATUS AND PROCESS FOR APPLYING DISCRETE PORTIONS OF A WEB MATERIAL ONTO RECEIVING WEB

The present invention relates to an apparatus and a process for applying discrete portions of a web material onto a receiving web. The apparatus and process are particularly useful in the manufacture of disposable absorbent articles, including diapers, adult incontinence products, sanitary napkins and the like.

Manufacturing processes are often required to provide discrete strips of a material onto a continuous web, in such a way that the discrete webs of material are spaced apart along the length of the continuous web. Features manufactured in this way include either elastic or non-elastic strips: one example of an elastic strip is the elastic leg cuffs applied to diapers; one example of a non-elastic strip is the absorbent core of a diaper or sanitary napkin which is typically constructed from air-laid fibres.

It is known to provide an apparatus for applying discrete portions of a web material onto a receiving web by supplying elastic strips to transfer members in a supply zone, the transfer members being rotated about a central axis. The transfer members are moved radially outwardly and then, in a transfer zone, the elastic strips are applied to the receiving web so that the elastic strips are transferred from the transfer members and onto the receiving web.

U.S. Pat. No. 4,578,133, issued Mar. 25, 1986, discloses a method and apparatus for applying elastic strips to a moving web of material by means of transfer members which move at a first orbital radius through the supply zone and at a second orbital radius through the transfer zone. Optionally the transfer-members may also be radially pivoted by pivoting the transfer member about an axis transverse to its strip carrying surface.

However, when the apparatus of the prior art are operated at high speed the contact between the transfer elements, the elastic strips and the receiving web occurs over a very brief period of time, usually no more then several milliseconds. This results in difficulties in achieve good reliable transfer of the strips from the transfer elements on to the receiving web.

It is an objective of the present invention to provide an apparatus wherein the contact time between the transfer elements, the elastic strips and the receiving web is increased.

SUMMARY OF THE INVENTION

The invention provides an apparatus for applying discrete portions of a web material onto a receiving web, comprising:
   a primary axis of rotation and an attachment zone at an average radial distance, $R_1$, from the primary axis of rotation;
   transfer elements rotatable about the primary axis, the transfer elements receiving a second web at a radial distance, $R_2$, from the primary axis wherein the radial distance $R_1$ is greater than the radial distance $R_2$;
   a means for displacing the transfer elements so that the second web is moved immediately adjacent to the attachment zone; and
   an attachment surface rotatable about the primary axis and through the attachment zone, for transporting the receiving web about the primary axis, whereby discrete portions of the second web is attached to the receiving web in the attachment zone, forming a composite web comprising the receiving web and discrete portions of the second web.

The invention further provides a process for applying discrete portions of a web material onto a receiving web, comprising the steps of:
   providing an attachment zone at an average radial distance, $R_1$, from a primary axis of rotation;
   providing a second web at a distance, $R_2$, from the primary axis, whereby the radial distance $R_1$ is greater than the radial distance $R_2$;
   displacing the second web at least in a radial direction relative to the primary axis so that the second web is displaced immediately adjacent to the attachment zone;
   juxtaposing the receiving web and the second web in the attachment zone to form a composite web comprising the receiving web and discrete portions of the second web; and
   transporting the receiving web about an arc of a circle, the circle having a primary axis and a first radius $R_1$.

BRIEF DESCRIPTION OF THE DRAWINGS

FIG. 5 shows a perspective view of an apparatus according to still another embodiment of the present invention.

DETAILED DESCRIPTION OF THE INVENTION

Figure 1:
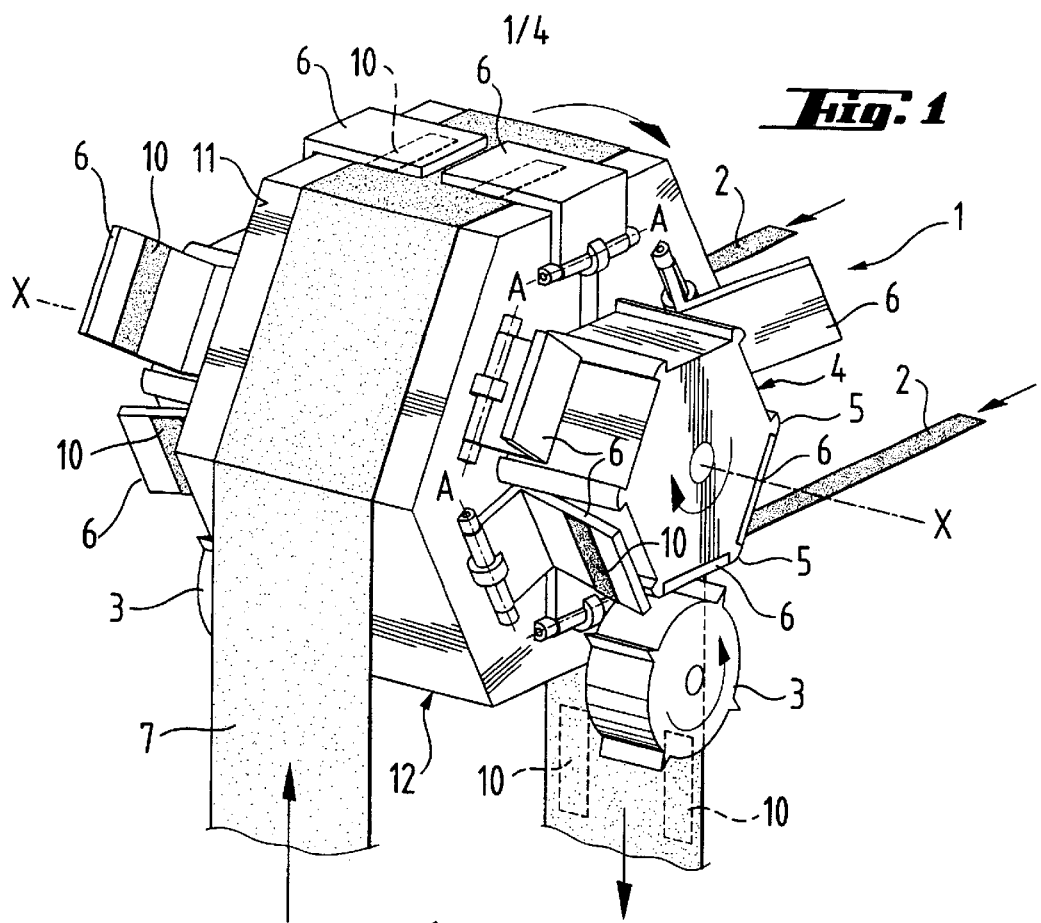
FIG. 1 shows a perspective view of an apparatus according to the present invention in which the secondary web is translated through 180° about a secondary axis.

It will be readily apparent to those skilled in the art that although the following description of the present invention is in connection with a single use diaper structure having discrete elastic regions or strips, the present invention may be practiced with equal facility on nearly any web.

It is preferred that the receiving web is a continuous web throughout the process of the present invention. In the following description a "continuous web" is a web of material which is continuous in the machine direction. A preferred continuous web comprises a plurality of interconnected single use disposable absorbent articles, such as diapers. Typically, each diaper is comprised of an absorbent pad element or absorbent core, and elastomeric elements or patches. The absorbent pad elements and the elastomeric elements are located between a backsheet and a topsheet, or alternatively, on top of a backsheet or topsheet. The continuous webs of backsheet material and topsheet material are preferably maintained under very slight tension in the machine direction to prevent wrinkling and to facilitate registration with the diaper assembly and converting operations until the completed diaper web is severed into discrete diapers by cutting across the width of the web. An alternative single use disposable absorbent article is a sanitary napkin or feminine hygiene pad.

The apparatus and process of the present invention provide a means for attaching discrete portions of one web onto a continuous receiving web. The discrete portions are intermittently spaced upon the receiving web by the apparatus and process of the present invention. The apparatus and process of the present invention provide "area contact" instead of "line contact" to the receiving web to transfer the discrete portions of another web material. This gives much longer process times to secure the discrete portions onto the receiving web. Moreover, it avoids extrusion effects either of the discrete portions or of the receiving web, which is important if they are soft and/or thick.

Another advantage of the apparatus of the present invention is in the fact that the discrete portions of web material and the receiving web are bent or shaped the same way when they are combined. This has advantages for several products, e.g. the combining step of feminine hygiene pads should be done such that the products are directly manufactured to the required body shape.

Preferably, the apparatus comprise a means for displacing the second web which comprises a plurality of segments, each segment being rotatable about a secondary axis wherein the secondary axis is orthogonal to the primary axis and does not intersect with the primary axis.

Even more preferably each rotatable segment receives a discrete portion of the second web, and the segment then rotates about the secondary axis through at least about 90°, and most preferably through about 180°, and juxtaposes the discrete portion of the second web against the receiving web in the attachment zone.

Figure 2:
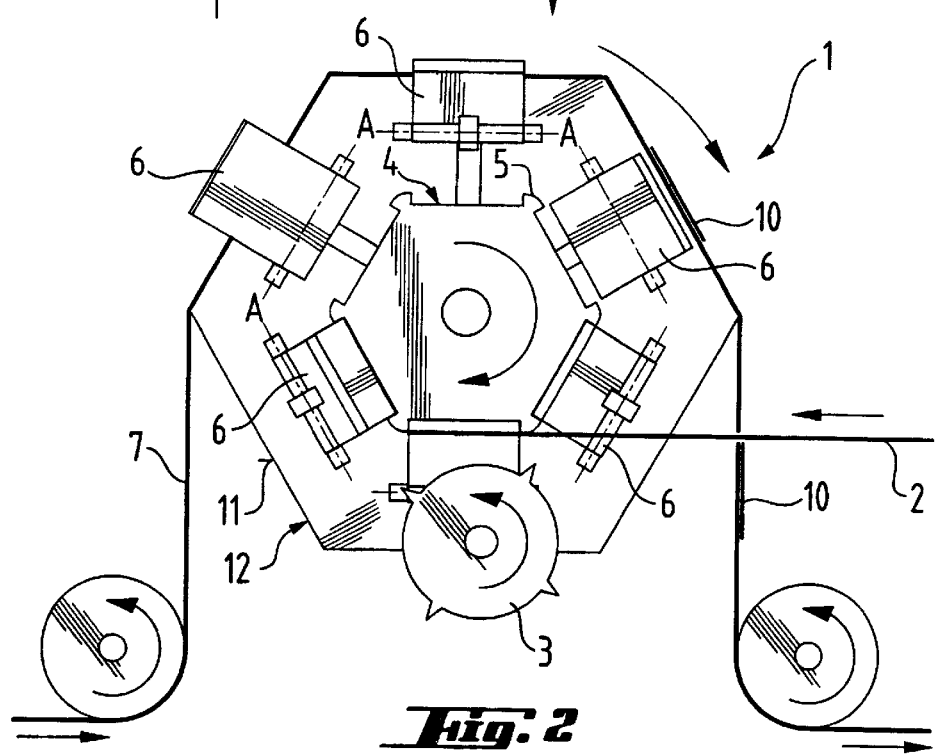
FIG. 2 shows a schematic plan view of the apparatus of FIG. 1.
Figure 3:
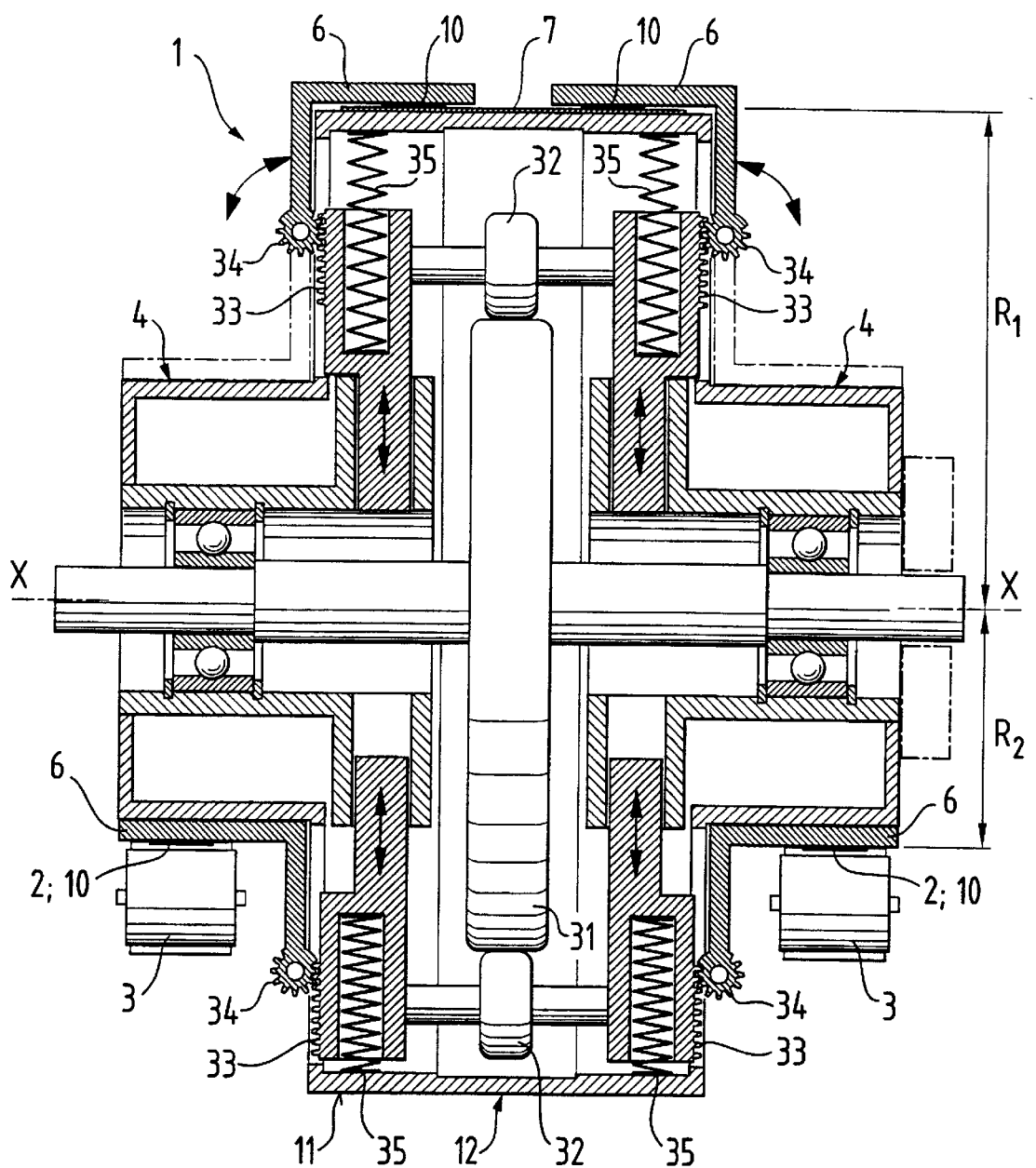
FIG. 3 shows a schematic side view of a mechanism in cross-section which is suitable for the apparatus embodied in FIG. 1.

FIGS. 1 to 3 illustrate a preferred embodiment of the present invention.

FIGS. 1 and 2 show an apparatus 1 and show a pair of webs 2 being fed into the apparatus. Each web 2 is fed towards an anvil drum 4 which, in this particular embodiment of the apparatus, is a hexagonal drum. The anvil drum comprises a plurality of anvils 5 (in this particular embodiment the hexagonal anvil drum 4 comprises six anvils 5). At the point of transfer of the incoming web 2 to the anvil drum 4, a transfer element 6 is interposed between the incoming web 2 and the anvil drum 4, and the incoming web is attached to the transfer-element 6 and cut into discrete portions 10 by a knife roll 3 acting against the anvil 5. As the anvil drum 4 is rotated about the primary axis of the apparatus, the transfer elements 6 are displaced by additionally rotating the transfer elements about a secondary axis, A—A. After a rotation of the transfer element 6 through 180° (which corresponds in the illustrated embodiment of FIG. 1 to a rotation of the anvil 4 about the primary axis of about 140°), the transfer element 6 is juxtaposed with a receiving web 7 in an attachment zone. The receiving web 7 is continuously fed onto the outer surface 11 of a hexagonal attachment drum 12. In the attachment zone the discrete portions 10 of the web 2 are transferred to, and attached to, the receiving web assisted by pressure applied between the transfer element 6 and the surface 10 attachment drum 12. As the apparatus 1 continues to rotate about the primary axis, the transfer element 6 rotates about the secondary axis in the opposite direction to the previous part of the cycle, so that after a rotation of 180° the transfer element 6 has returned to its original position and is interposed between the anvil 4 and the incoming web 2. The cycle is now ready to repeat.

FIGS. 1 and 2 illustrate a hexagonal anvil drum 4, a hexagonal attachment drum 12, and six pairs of transfer elements 6. Of course the apparatus, could equally well consist of an octagonal anvil drum, and octagonal attachment drum, and eight pairs of transfer elements; or any other desired number of transfer elements. Furthermore, whilst FIG. 1 shows pairs of transfer elements 6 disposed on either side of the apparatus 1, the apparatus 1 may only be fitted with one set of transfer elements 6 on one side of the apparatus 1.

FIG. 3 shows a cross section of an apparatus 1 according to the present invention. The attachment drum 12 rotates about the primary axis of the apparatus 1. A cam 31 is mounted within the attachment drum 12 to guide an oscillating mechanism 32 which is provided with a rack 33. The rack cooperates with a pinion 34 which is linked to the pivotally mounted transfer element 6. When the oscillating mechanism 32 is in the position indicated in the lower part of FIG. 3, the transfer elements 6 are in position ready to receive the incoming-web 2 at an average radial distance $R_2$ from the principal axis. Knife rolls 3 cut the web 2 into discrete portions. As the apparatus 1 rotates about the principal axis, the oscillating mechanism 32 is pushed inwards, towards from the principal axis, by means of resilient members, such as springs 35. The rack and pinion 33, 34 cause the transfer elements 6 to rotate about a secondary axis. When the oscillating mechanism 32 is in the position indicated in the upper part of FIG. 3, the transfer elements 6 have moved through 180° about the secondary axis into the attachment zone and the discrete portions of the web are transferred to the receiving web on the outer surface 11 of the attachment drum 12 at an average radial distance $R_1$ from the principal axis.

Figure 4:
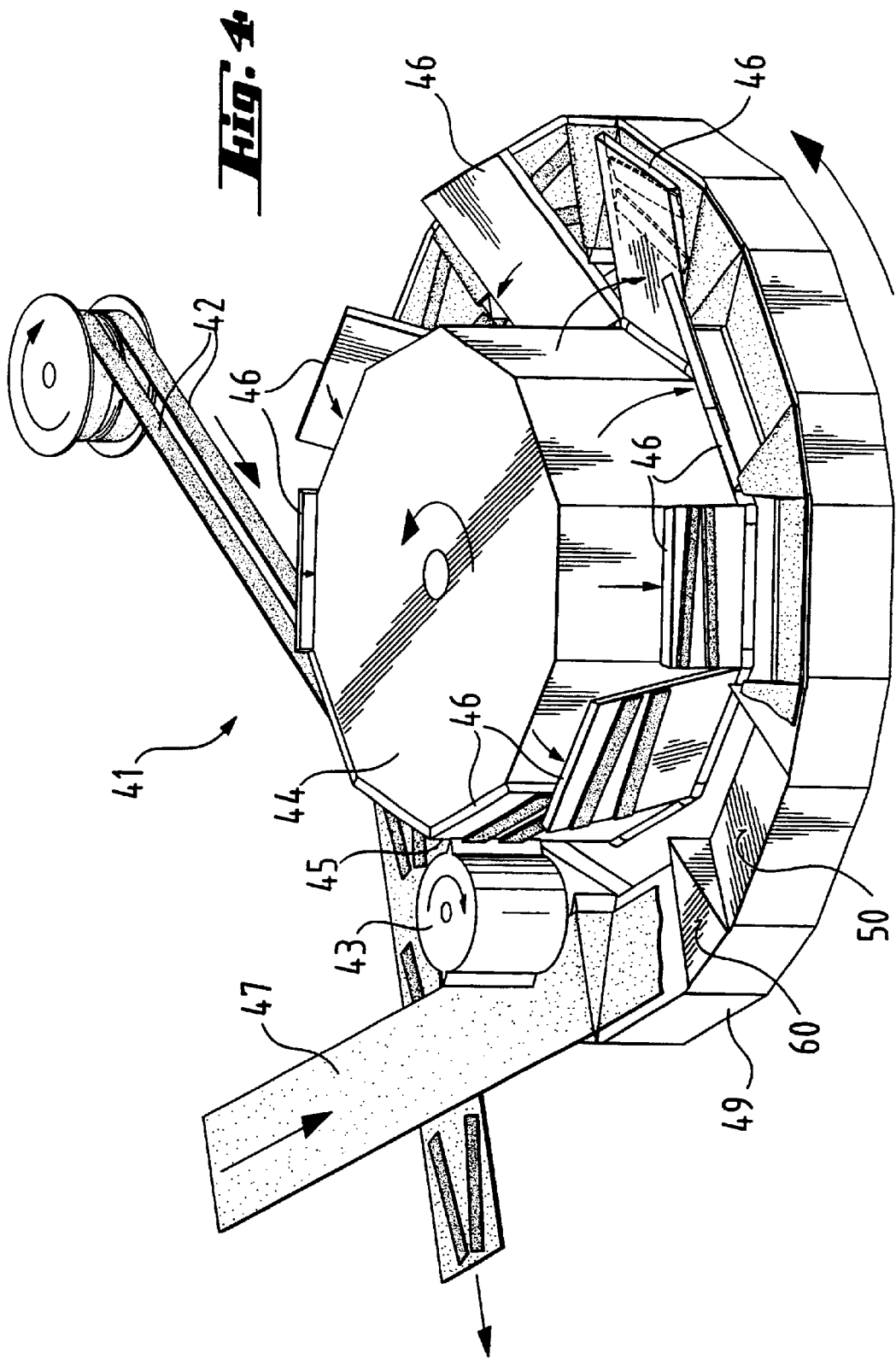
FIG. 4 shows a perspective view of an apparatus according to another embodiment of the present invention in which the secondary web is translated through 90° about the secondary axis.

FIGS. 4 and 5 illustrate alternative embodiments of the present invention.

FIG. 4 shows an apparatus 41 according to an alternative embodiment of the present invention. FIG. 4 shows a pair of webs 42 being fed into the apparatus. Each web 42 is fed towards an anvil 44 which, in this particular embodiment of the apparatus, is a ten-sided drum. At the point of transfer of the incoming web 42 to the anvil 44, a transfer element 46 is interposed between the incoming web 42 and the anvil 44, and the incoming web is attached to the transfer element 46 and cut into discrete portions by a knife roll 43 acting against the anvil 45. As the anvil drum 44 is rotated about the primary axis, the transfer elements 46 are displaced by additionally rotating the transfer elements about a secondary axis. After a rotation of the transfer element 46 through 90° (which corresponds in the illustrated embodiment of FIG. 4 to a rotation of the anvil 44 about the primary axis of about 140°), the transfer element 46 is juxtaposed with a receiving web 47 in an attachment zone. The receiving web 47 is continuously fed onto the flange of an attachment drum 49. In order to accommodate the linear receiving web 47 around the circular path of the flange 49 of the attachment drum, a series of "hold-down" sections and compensation triangles are provided as illustrated in FIG. 4. In the attachment zone the discrete portions of the web 42 are transferred to, and attached to, the "hold-down" section of the receiving web 47 assisted by pressure applied between the transfer element 46 and the flange 49 of the attachment drum. As the apparatus 41 continues to rotate about the primary axis, the transfer element 46 rotates about the secondary axis in the opposite direction to the previous part of the cycle, so that after a rotation of 90° about the secondary axis the transfer element 46 has returned to its original position and is interposed between the anvil 44 and the incoming web 42. The cycle is now ready to repeat.

FIG. 5 shows an apparatus 51 according to another alternative embodiment of the present invention. FIG. 5 shows a of web 52 being fed into the apparatus. The web 52 is fed towards an anvil drum 54. At the point of transfer of the incoming web 52 to the anvil 54, a transfer element 56 is interposed between the incoming web 52 and the anvil 54 the incoming web is attached to the transfer element 56 and cut into discrete portions by a knife roll 53 acting against the anvil 55. As the anvil drum 55 is rotated about the primary axis, the transfer elements 56 are displaced both parallel to the primary axis as well as radially away from the primary axis, the displacement being indicated by arrows in FIG. 5, into an attachment zone. The attachment zones lie in a series of apertures in the outer surface of the attachment drum 59. The discrete portions of the web 52 are bonded to the receiving web 57 by means of pressure applied by a bonding roll 58 located outside of the path of the receiving web 57, acting upon the displaced transfer element 6. The transfer elements 56 are subsequently displaced back to their original position so that the cycle can be repeated.

In an optional aspect of the invention, glue can be applied either to the knives or to the anvil of any embodiment of the invention, before the second web is cut into discrete portions. When the second web is cut into discrete portions, glue is transferred to the ends of the discrete portions which provides for efficient sealing of the cut ends of the discrete portions with a very small amount of glue.

What is claimed is:

1. A process for applying discrete portions (10) of a web material onto a receiving web (7), comprising the steps of:

providing an attachment zone at an average radial distance, $R_1$, from a primary axis of rotation;

providing a second web (2) at a distance, $R_2$, from the primary axis, whereby the radial distance $R_1$ is greater than the radial distance $R_2$;

displacing the second web (2) at least in a radial direction relative to the primary axis so that the second web (2) is displaced immediately adjacent to the attachment zone;

juxtaposing the receiving web (7) and the second web (2) in the attachment zone to form a composite web comprising the receiving web (7) and discrete portions (10) of the second web (2), wherein discrete portions (10) are formed by cutting the second web (2);

characterised in that the process further comprises the step of transporting the receiving web about a path lying essentially in the arc of a circle, the essentially circular path at radius $R_1$ from the primary axis of rotation, wherein the entire discrete portions (10) of the second web (2) are displaced in an axial direction, in addition to the translation in the radial direction, relative to the primary axis.

2. A process according to claim 1 wherein the discrete portions (10) of the second web (2) are displaced about a secondary axis, wherein the secondary axis is orthogonal to the primary axis and does not intersect with the primary axis.

3. A process according to claim 2 wherein the discrete portions (10) of the second web (2) are translated through at least about 90° about the secondary axis.

4. A process according to claim 1 wherein the cutting step is carried out by means of the action of a knife upon an anvil, and wherein the surface of either or both of the knife and anvil have glue applied to them before the cutting step.

5. An apparatus (1) for applying discrete portions (10) of a web material onto a receiving web (7), comprising:

a primary axis of rotation and an attachment zone at an average radial distance, $R_1$, from the primary axis of rotation;

transfer elements (6) rotatable about the primary axis, the transfer elements receiving a second web (2) at a radial distance, $R_2$, from the primary axis wherein the radial distance $R_1$ is greater than the radial distance $R_2$;

a means for displacing the transfer elements (6) so that the second web (2) is moved immediately adjacent to the attachment zone;

a means (3, 5) for cutting the second web (2) into discrete portions (10); characterised in that the apparatus further comprises an attachment surface (10) rotatable about the primary axis and through the attachment zone, for transporting the receiving web (7) about the primary axis, whereby discrete portions (10) of the second web (2) are attached to the receiving web (7) on the attachment zone, forming a composite web comprising the receiving web (7) and discrete portions (10) of the second web (2), wherein the average radial distance, $R_1$, is substantially the same over the entire attachment surface.

6. An apparatus according to claim 5 wherein the means for displacing the second web (2) comprises a plurality of segments, each segment being rotatable about a secondary axis wherein the secondary axis is orthogonal to the primary axis and does not intersect with the primary axis.

7. An apparatus according to claim 6 wherein each rotatable segment receives a discrete portion (10) of the second web (2), and wherein in segment rotates about the secondary axis through at least about 90°, and juxtaposes the discrete portion (10) of the second web (2) against the receiving web (7) in the attachment zone.

* * * * *

UNITED STATES PATENT AND TRADEMARK OFFICE
CERTIFICATE OF CORRECTION

PATENT NO. : 6,656,312 B1
DATED : December 2, 2003
INVENTOR(S) : Schmitz et al.

It is certified that error appears in the above-identified patent and that said Letters Patent is hereby corrected as shown below:

<u>Title page,</u>
Item [57], ABSTRACT
Line 5, delete "transfer elements (6) rotatable about the axis" and insert -- transfer elements (6) rotatable about the primary axis --.

<u>Column 1,</u>
Line 33, delete "transfer-members" and insert -- transfer members --.

<u>Column 3,</u>
Line 39, delete "transfer-element" and insert -- transfer element --.

<u>Column 4,</u>
Line 13, delete "incoming-web" and insert -- incoming web --.

Signed and Sealed this

Fifteenth Day of June, 2004

JON W. DUDAS
*Acting Director of the United States Patent and Trademark Office*